United States Patent
Slagel (10) Patent No.: US 8,877,487 B2
(45) Date of Patent: Nov. 4, 2014

(54) PHOTOBIOREACTOR AND A PROCESS FOR ENHANCING GROWTH OF PHOTOSYNTHETIC ORGANISMS

(76) Inventor: David D. Slagel, Goshen, IN (US)

(*) Notice: Subject to any disclaimer, the term of this patent is extended or adjusted under 35 U.S.C. 154(b) by 1054 days.

(21) Appl. No.: 12/804,991

(22) Filed: Aug. 3, 2010

(65) Prior Publication Data
US 2011/0033912 A1   Feb. 10, 2011

Related U.S. Application Data

(60) Provisional application No. 61/231,304, filed on Aug. 4, 2009.

(51) Int. Cl.
- C12M 1/42 (2006.01)
- C12N 1/12 (2006.01)
- A01H 4/00 (2006.01)
- C12M 1/00 (2006.01)
- C12M 1/06 (2006.01)

(52) U.S. Cl.
CPC C12N 1/12 (2013.01); A01H 4/001 (2013.01); C12M 21/02 (2013.01); C12M 23/22 (2013.01); C12M 27/02 (2013.01); C12M 27/18 (2013.01); C12M 29/14 (2013.01)
USPC ............. 435/292.1; 435/296.1; 366/102; 366/332; 47/1.4

(58) Field of Classification Search
CPC ...... C12M 21/02; C12M 23/22; C12M 23/56; C12M 27/02; C12M 27/04; C12M 29/06; C12M 29/08; C12M 27/18; C12M 29/14; A01H 4/001; B01F 2003/04141
USPC ........ 435/292.1, 296.1; 47/1.4; 366/101, 102, 366/332

See application file for complete search history.

(56) References Cited

U.S. PATENT DOCUMENTS

| | | | |
|---|---|---|---|
| 2,815,607 A | 12/1957 | Schroeder | |
| 4,595,296 A * | 6/1986 | Parks | ............. 366/106 |
| 4,676,956 A | 6/1987 | Mori | |
| 4,724,214 A | 2/1988 | Mori | |
| 4,900,678 A | 2/1990 | Mori | |
| 4,952,511 A | 8/1990 | Radmer | |
| 6,036,357 A * | 3/2000 | Van Drie | ............. 366/332 |
| 6,348,347 B1 | 2/2002 | Hirabayashi et al. | |
| 6,602,703 B2 | 8/2003 | Dutil | |
| 2007/0091716 A1 * | 4/2007 | Zeikus | ............. 366/104 |
| 2007/0264708 A1 | 11/2007 | Bayless et al. | |

* cited by examiner

*Primary Examiner* — William H Beisner
(74) *Attorney, Agent, or Firm* — Mark E. Wiemelt (57) ABSTRACT

A photobioreactor apparatus in which a reaction chamber contains a slurry of water, nutrients and photosynthetic organisms. The sidewall of the reaction chamber is constructed of translucent material, thereby permitting light to be conveyed into the slurry to promote photosynthesis. The interior of the reaction chamber is in fluid communication with a gas dispenser. A lift member is disposed in the reaction chamber and gas is introduced in the slurry beneath the lift member, thereby providing buoyancy to lift the lift member, thereby providing agitation and movement of the slurry within the photobioreactor and enhancing growth of photosynthetic organisms.

5 Claims, 6 Drawing Sheets

PHOTOBIOREACTOR AND A PROCESS FOR ENHANCING GROWTH OF PHOTOSYNTHETIC ORGANISMS

CROSS-REFERENCE TO RELATED APPLICATIONS

This application claims the benefit of priority to U.S. Provisional patent application Ser. No. 61/231,304, filed Aug. 4, 2009, which is incorporated herein by reference.

FIELD OF THE INVENTION

The present invention relates generally to the field of photobioreactors.

More particularly, it concerns a photobioreactor and a process for enhancing growth of photosynthetic organisms, such as microalgae for commercial production.

BACKGROUND OF THE INVENTION

It is well known that fossil fuels, such as petroleum-derived fuels and coal, are limited in supply. Additionally, the combustion of such fuels contributes substantial carbon to the atmosphere. The release of carbon long stored in such fuels is the subject of global concern relating to climate change and other environmental problems. Nevertheless, fossil fuels are the largest fuel source for automobiles and energy production facilities.

Biofuels are derived from recently living organisms or their metabolic byproducts, but contain different hydrogen and carbon containing molecules than fossil fuels. Biofuels contain sufficient enthalpy to compete with fossil fuels for vehicle fuel and energy production. Most biofuels are considered neutral in their release of carbon into the atmosphere, because the living organisms remove carbon from the air, but that carbon is subsequently released during the chemical reaction that produces work from the stored solar energy.

Biofuels are a renewable energy source, unlike other natural resources such as petroleum, coal, and nuclear fuels. Some biofuels can be grown in a conventional setting, such as a farm field, while others must be grown in unique, controlled settings. A photobioreactor is a vessel in which a chemical process is carried out that involves organisms or biochemically active substances derived from such organisms. Known photobioreactors take the exhaust gases of, for example, fossil fuel burning power plants, and use the $CO_2$ therein to facilitate growth of microalgae and other photosynthetic organisms. Such photobioreactors prevent carbon from the exhaust gas stream from being released into the air, and produce biofuel therefrom that provides additional energy. Open-pond photobioreactor systems have existed for some time, but are unsuitable in many ways, especially for large sources of $CO_2$.

Microalgae have much faster growth-rates than terrestrial crops. Depending on the photobioreactor and the strain, the per unit area yield of oil from algae is estimated to be many times greater than the next best crop, which is palm oil. Algal-oil processes into biodiesel as easily as oil derived from land-based crops. The difficulties in efficient biodiesel production from algae lie in finding a cost-effective photobioreactor that is best suited to a strain of algae that contains sufficient lipids.

Research into algae for the mass-production of fuel is mainly focused on microalgae, as opposed to macroalgae (seaweed). Microalgae are organisms capable of photosynthesis that are less than 2 mm in diameter. These include the diatoms and cyanobacteria. This preference towards microalgae is due largely to its less complex structure, fast growth rate, and high oil content in some species.

Despite the scientific advantages of biofuels and the availability of photobioreactors that are capable of producing such fuels, economic disadvantages have restricted the extent to which photobioreactors have been implemented. For example, one disadvantage of conventional photobioreactors is the fact that space is not always available where large supplies of $CO_2$ are being produced. Biofuels produced from such photobioreactors can only compete with petroleum-based fuels if their production is high enough that economies of scale exist. This is difficult with conventional photobioreactors.

The production of microalgae as a feedstock for refining into biodiesel requires photobioreactors that are capable of maximum productivity in minimum space and with minimal energy inputs.

Therefore, the need exists for a photobioreactor and process that makes biofuel production economically feasible enough that it will be adopted by the energy producing industry.

BRIEF SUMMARY OF THE INVENTION

The photobioreactor of the invention addresses significant problems of conventional photobioreactor designs. The invention uses pressurized gas introduced in a slurry beneath a lift member to provide buoyancy to lift the lift member, thereby providing agitation and movement of the slurry within the photobioreactor, thereby enhancing growth of photosynthetic organisms.

The photobioreactor of the invention is suitable for the enhanced growth of any kind of photosynthetic organism, such as plant cells and unicellular or multicellular organisms having light and agitation requirements. As used herein, the term "photosynthetic organisms" also includes organisms genetically modified by techniques well known to one skilled in the art.

The photobioreactor apparatus includes a reaction chamber that contains a slurry of water, nutrients and photosynthetic organisms. The sidewall of the reaction chamber is constructed of transparent material, thereby permitting light to be conveyed into the slurry to promote photosynthesis. The interior of the reaction chamber is in fluid communication with a pressurized gas dispenser. A lift member is disposed in the reaction chamber and pressurized gas is introduced in the slurry beneath the lift member, thereby providing buoyancy to lift the lift member, thereby providing agitation and movement of the slurry within the photobioreactor and enhancing growth of photosynthetic organisms.

The invention provides innovative features that integrate several steps in the photosynthetic organisms growth process so that the same energy can be used for multiple processes. The invention greatly reduces overall energy demands of the process. The invention creates a scalable platform for the commercial growth of organisms. One goal is to use the introduction of gas, such as $CO_2$, to both "fuel" growth of the organisms and to facilitate agitation of the liquid further promote growth and to minimize self shading of the organisms allowing organisms to be grown in light conditions to an economically harvestable concentration. There has been outlined, rather broadly, the more important features of the invention in order that the detailed description thereof that follows may be better understood, and in order that the present contribution to the art may be better appreciated.

There are, of course, additional features of the invention that will be described hereinafter and that will form the subject matter of the invention.

As such, those skilled in the art will appreciate that the conception, upon which this disclosure is based, may readily be utilized as a basis for designing of other structures, methods, and systems for carrying out the several purposes of the present invention. It is important, therefore, that the claims be regarded as including such equivalent constructions in so far as they do not depart from the spirit and scope of the present invention.

For a non-limiting example, it is readily apparent that the inventive device could be made in a variety of ways as long as the pressurized gas is introduced in the slurry beneath the lift member to provide buoyancy to lift the lift member.

Further, the purpose of the abstract is to enable the US patent and trademark office and the public generally, and especially the scientists, engineers and practitioners in the art who are not familiar with the patent or legal terms or phraseology, to determine quickly from what cursory inspection the nature and essence of the technical disclosure of the application. The abstract is neither intended to define the invention of the application, which is measured by the claims, nor is it intended to be limiting as to the scope of the present invention in any way.

These together with other objects of the present invention, along with the various features of novelty which characterize the present invention, are pointed out with particularity in the claims annexed to and forming a part of this disclosure. For a better understanding of the present invention, its operating advantages and the specific objects attained by its uses, reference should be had to the accompanying drawings and descriptive matter in which there is illustrated a preferred embodiment of the present invention.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose. For example, the word connected or terms similar thereto are often used. They are not limited to direct connection, but include connection through other elements where such connection is recognized as being equivalent by those skilled in the art.

DESCRIPTION OF ILLUSTRATIVE EMBODIMENTS

Illustrative embodiments of the invention are described below as they might be employed. In the interest of clarity, not all features of an actual implementation are described in this specification. It will of course be appreciated that in the development of any such actual embodiment, numerous implementation specific decisions must be made to achieve the developers' specific goals which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments of the invention will become apparent from consideration of the following description and drawings.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Embodiments of the invention will now be described with reference to the accompanying figures.

The preferred embodiment of the present invention is shown in FIGS. 1-5, in which the photobioreactor 10 is shown in a preferred configuration. The preferred configuration of the photobioreactor 10 includes a reaction chamber 12, a base 18, a lift member 40, a pressurized gas dispenser 50, and a stabilizing member 60.

The reaction chamber 12 of the preferred embodiment is preferably a cylindrical tube having a sidewall 14. The sidewall 14 is connected generally perpendicularly to a floor 16, although it should be apparent that they may be integrally formed. The reaction chamber 12 is preferably approximately 32 inches in diameter, and approximately 65 inches tall. The sidewall 14 is preferably made of an inert, transparent plastic material, such as acrylic or polycarbonate. It should be apparent that the sidewall 14 may also be translucent. In the preferred embodiment of the present invention, the reaction chamber 12 has an annular lip 20 extending generally radially outwardly from the top of the sidewall 14. The floor 16 is preferably made of an inert plastic material, but it should be apparent that it does not have to be made of plastic. The floor 16 also does not have to be transparent. It should also be apparent that the material of which the reaction chamber 12 is made must be strong enough to contain a water and algae slurry.

The reaction chamber 12 is preferably disposed on a base 18, which may be rectangular in shape and sized so that it substantially underlays the reaction chamber 12 and provides stability thereto. The base 18 is preferably made of a generally rigid plastic material, but it should be apparent that it does not have to be made of plastic.

The pressurized gas dispenser 50 of the preferred embodiment of the present invention includes a conduit 32 which is in fluid communication therewith. The pressurized gas dispenser 50 contains a fluid (not shown), preferably a gas, such as $CO_2$, either in pure form or in a slurry. The pressurized gas dispenser 50 preferably is supplied by the exhaust from fossil fuel combustion, such as a coal-burning power plant, natural gas burning power plant, gasoline internal combustion engine, a water gas shift reactor or any other carbon-laden gas producing apparatus. Alternatively, the source of gas can be any apparatus that produces gas containing elements and/or compounds that can be utilized by photosynthetic organisms. The conduit 32 is also in fluid communication with the interior of the reaction chamber 12 and terminates below the lift member 40. A valve (not shown) is interposed in the conduit 32 for providing selective fluid communication of the gas dispenser 50 with the reaction chamber 12. In the preferred embodiment of the present invention, the conduit 32 is preferably an extendable hose that extends from above the reaction chamber 12 and vertically downwardly through the interior of the reaction chamber 12, terminating below the lift member 40.

The stabilizing member 60 of the preferred embodiment is preferably a cylindrical tube having a sidewall 62 at least as large in diameter as that of the sidewall 14 of the reaction chamber 12 and having a generally tubular stabilizer sleeve 66 disposed generally radially centrally therein and a plurality of generally planar ribs 64 which extend generally radially and are connected between the sidewall 64 of the stabilizing member 60 and the stabilizer sleeve 66, such as by adhesive or fasteners (not shown), although it should be apparent that they may be integrally formed. Of course, any suitable adhesive or fastener can be used. The stabilizer sleeve 66 preferably extends generally vertically above the ribs 64 and terminates proximate the bottom of the ribs 64, although it should be understood that it need not extend above the ribs 64 and it may terminate above or below the bottom of the ribs 64. It is preferred that the ribs 64 be spaced generally at equidistant intervals from each other. In the preferred embodiment, the stabilizing member 60 is disposed generally vertically above, rests upon, and is connected to the annular lip 20 of the reaction chamber 12, although it should be understood that the stabilizing member 60 may be disposed generally vertically above, rest upon, and be connected to the reaction chamber 12 in the absence of the annular lip 20. It should also be understood that the stabilizing member 60 need not rest upon or be connected to the reaction chamber 12. The stabilizing member 60 is preferably made of an inert plastic material, such as acrylic or polycarbonate, but it should be apparent that it does not have to be made of plastic. It should also be apparent that all or part of the stabilizing member 60 may also be transparent or translucent.

The lift member 40 of the preferred embodiment has a generally truncated conical shape and a generally tubular lift element 42 disposed generally radially centrally thereon and extending generally vertically upwardly therefrom and a plurality of generally planar ribs 64 which extend generally radially inwardly and downwardly from the interior surface of the lift member 40 and which are connected to the lift member 40, such as by adhesive or fasteners (not shown), although it should be apparent that they may be integrally formed. Of course, any suitable adhesive or fastener can be used. In the preferred embodiment, the lift element 42 is connected to the lift member 40 by adhesive (not shown), although it should be apparent that they may be integrally formed. Of course, any suitable adhesive or fastener can be used. In the preferred embodiment, the lift member 40 is sized to extend radially outwardly proximate the sidewall 14 of the reaction chamber 12 to provide a close fit therewith so that it channels the photosynthetic organisms toward the sidewall 14 during upward translation of the lift member 40. The lift element 42 extends generally vertically above the lift member 40 and is sized to be effectively sealably and slidably received within the stabilizer sleeve 66 and adapted to be reciprocated therein, thereby allowing vertical translation of the lift member 40. In the preferred embodiment, the tubular lift element 42 also extends vertically downwardly from the interior surface of the lift member 40. In the preferred embodiment, the tubular lift element 42 terminates proximate the bottom of the lift member 40. Alternatively, the tubular lift element 42 may solid, capped, plugged, or otherwise sealed to prevent escape of gas vertically therethrough. It is preferred that the ribs 44 be spaced generally at equidistant intervals from each other. The lift member 40 is preferably made of an inert plastic material, such as acrylic or polycarbonate, but it should be apparent that it does not have to be made of plastic. It should also be apparent that all or part of the lift member 40 may also be transparent or translucent. It should also be apparent that the lift member 40 may generally be of type including a concave portion, such as domed shape, a conical shape, or a cylindrical shape of a closed type, or any other shape that will trap gas that is introduced below lift member 40. In the preferred embodiment, the ribs 64 and lift member 12 are configured to allow the lift member 12 to be translated vertically upwardly into generally mirrored or seated engagement with the bottom of the stabilizer member 60. The lift member 40 of the preferred embodiment has a plurality of discharge valves 46 that may be selectively activated to allow gas which is trapped below the lift member 40 to be released.

Figure 1:
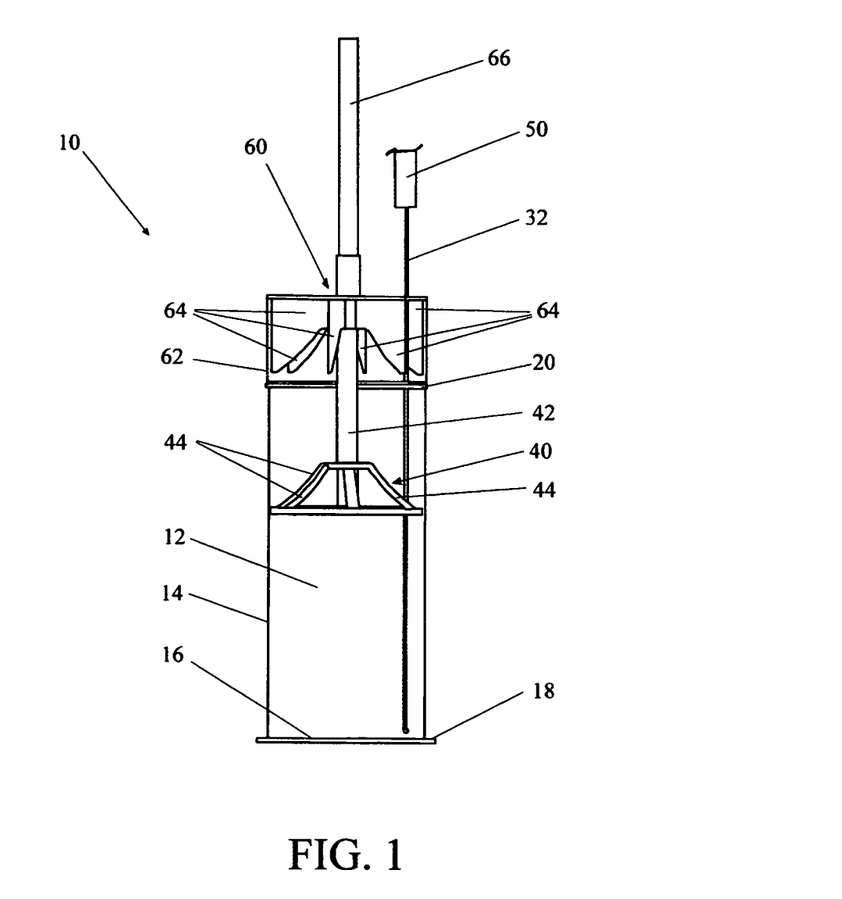
FIG. 1 is a front view illustrating a preferred embodiment of the present invention with a front portion of the sidewall of the reaction chamber and a front portion of the sidewall of the stabilizing member cutaway.
Figure 2:
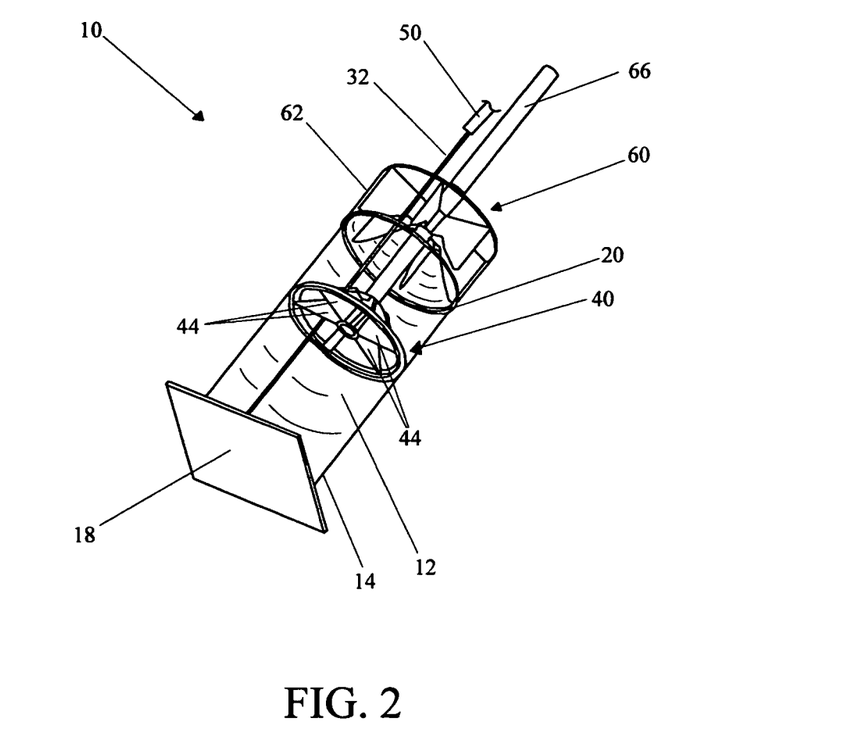
FIG. 2 is a rear perspective view illustrating a preferred embodiment of the present invention with a rear portion of the sidewall of the reaction chamber and a rear portion of the sidewall of the stabilizing member cutaway.
Figure 3:
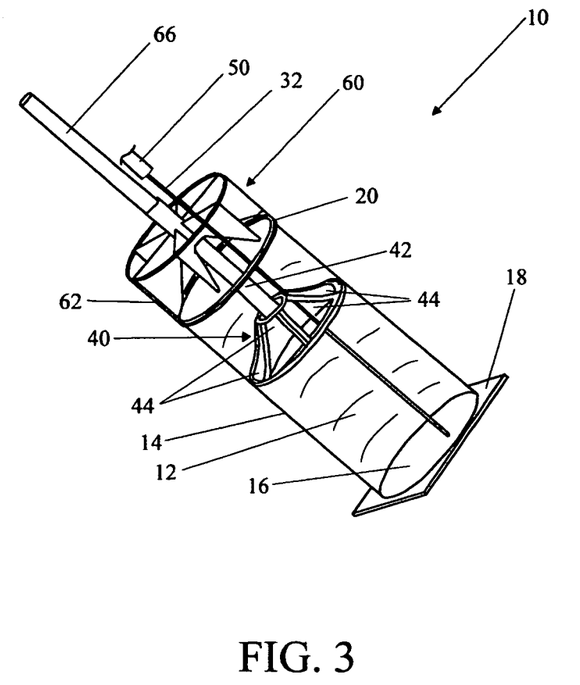
FIG. 3 is a front perspective view illustrating a preferred embodiment of the present invention with a front portion of the sidewall of the reaction chamber and a front portion of the sidewall of the stabilizing member cutaway.
Figure 4:
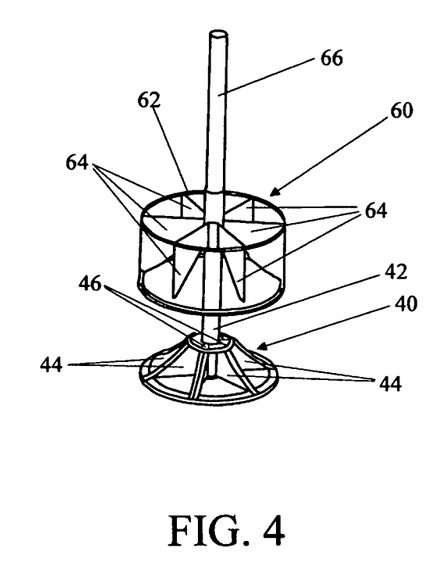
FIG. 4 is a perspective view illustrating the lift member and stabilizing member of a preferred embodiment of the present invention.
Figure 5:
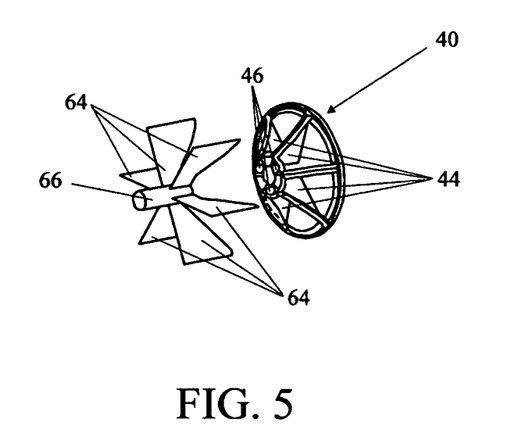
FIG. 5 is a perspective view illustrating the ribs and stabilizer sleeve of the stabilizing member and the lift member of a preferred embodiment of the present invention.
Figure 6:
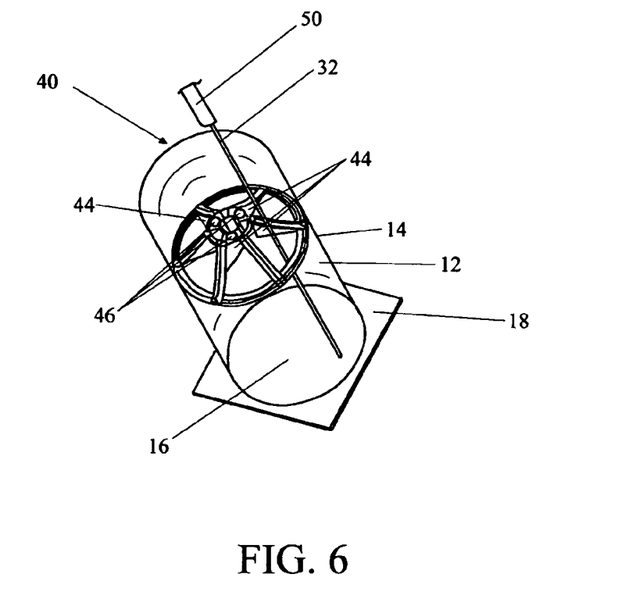
FIG. 6 is a front perspective view illustrating an alternate embodiment of the present invention with a front portion of the sidewall of the reaction chamber cutaway.

A alternative embodiment of the present invention is shown in FIG. 6, in which the photobioreactor 10 is shown. This alternative embodiment does not include a stabilizing member 60, an annular lip 20, or a lift element 42, and the aperture through which the lift element 42 of the preferred embodiment extends is not present. Otherwise, this alternative embodiment is the same as the preferred embodiment described above.

The process of the present invention provides agitation and movement of a slurry within a photobioreactor, thereby enhancing growth of photosynthetic organisms. In operation, a slurry of water, nutrients and photosynthetic organisms is introduced into the interior of the reaction chamber 12. The slurry may be introduced by any known means, such as by a pump, gravity, etc. Other materials, such as nutrients, and contaminants can be in the reaction chamber 12, but preferably these comprise a small fraction of the contents of the reaction chamber 12. A pressurized gas is introduced into the interior of the reaction chamber 12 beneath the lift member 40, thereby forming many small bubbles and creating turbulence in the water in the reaction chamber 12. This turbulence agitates the slurry, thereby facilitating growth of photosynthetic organisms. Enough pressurized gas is introduced in the slurry beneath the lift member 40 sufficient to provide buoyancy to lift the lift member 40.

After completion of an upward stroke, discharge valves 46 may be selectively activated to allow gas which is trapped below the lift member 40 to be released. Upon release of the trapped gas, it should be understood that gravity will lower the lift member 40 in the reaction chamber 12, thereby providing further turbulence and agitating the slurry. The cycle of upward stroke and downward stroke of the lift member 40 may be repeated.

At various points during the cycle of upward stroke and downward stroke, the photosynthetic organisms may be harvested by any known means, such as by filtering or scraping.

In preferred operation, three types of algae that are contemplated for use in the photobioreactor are AMPHO 46 (Amphora (diatom)), OOCYS 09 (Oocystis (green algae, Chlorophyta)) and SYNEC 05 (Synecococcus (cyanobacterium)). Of course, it is contemplated that other, naturally-existing organisms can be used, and that organisms can be modified to work more effectively. For the production of biofuels, such as biodiesel, it is desirable to use algae that produces the most lipids as fast as is feasible. Of course, for the production of other nutraceuticals, pharmaceutical compound or other nutritional compounds, different organisms are contemplated. For the production of ethanol and butinol, among others, high starch organisms may be more desirable. By circulating the water/algae slurry using carbon dioxide ($CO_2$) gas that the algae absorb, growth of the algae is enhanced.

The photobioreactor has enhanced algal productivity for the purpose of producing a high-lipid feedstock for biodiesel refining. Of course, the algae or other photosynthetic microorganism can be used for other purposes, including, but not limited to, other biofuels, nutrition and carbon sequestration.

It will be understood that although the photobioreactor 10 of the present invention preferably has a generally cylindrical configuration, it is recognized that any suitable shape may be used. For instance, the present invention also contemplates employing a hexagon-shaped, cubic-shaped, or rectangular photobioreactor, including the reaction chamber 12, the lift member 40 and the stabilizer member 60, and their component parts. A person skilled in the art will also understand that the volume of the photobioreactor 10 can easily be manipulated by simply modifying the dimensions of its components.

Even though the process of the invention as described previously uses only one photobioreactor 10, it will be clear to one skilled in the art from the following example that it is conceivable to use more than one photobioreactor 10 so as to greatly increase the production capacity of the process contemplated by the present invention.

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention.

This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

What is claimed is:

1. A photobioreactor apparatus comprising:
a photosynthesis reaction chamber having a floor and at least one transparent sidewall, said reaction chamber containing a slurry comprising liquid and photosynthetic organisms;
a lift member disposed within said reaction chamber,
a stabilizer member having a tubular stabilizer sleeve; and
a pressurized gas dispenser containing a gas, said reaction chamber being in fluid communication with said gas dispenser, wherein said gas is introduced in the slurry beneath said lift member, thereby providing buoyancy to lift said lift member, thereby providing agitation and movement of the slurry within the photobioreactor and enhancing growth of photosynthetic organisms, wherein said stabilizer member comprises a cylindrical tube having a sidewall at least as large in diameter as that of said sidewall of said reaction chamber, said stabilizer member disposed generally radially centrally on said reaction chamber, and a plurality of generally planar ribs which extend generally radially and are connected between said sidewall of said stabilizing member and said stabilizer sleeve.

2. The photobioreactor apparatus of claim 1 further comprising a generally tubular lift element disposed generally radially centrally on said lift member and extending generally vertically upwardly therefrom.

3. The photobioreactor apparatus of claim 2, wherein said lift element is sized to be effectively sealably and slidably received within said stabilizer sleeve and adapted to be reciprocated therein, thereby allowing vertical translation of said lift member.

4. The photobioreactor apparatus of claim 3, wherein said stabilizing member and said lift member are configured to allow said lift member to be translated vertically upwardly into generally mirrored or seated engagement with the bottom of said stabilizer member.

5. The photobioreactor apparatus of claim 4, wherein sidewall of said reaction chamber is transparent.

* * * * *